(12) United States Patent
Perry

(10) Patent No.: US 8,419,698 B2
(45) Date of Patent: Apr. 16, 2013

(54) ECO-FRIENDLY URINE GUARD FOR SHIELDING AND/OR RECEIVING DISCHARGING URINE FROM AN INFANT

(76) Inventor: Patricia A. Perry, Fishers, IN (US)

( * ) Notice: Subject to any disclaimer, the term of this patent is extended or adjusted under 35 U.S.C. 154(b) by 631 days.

(21) Appl. No.: 12/207,786

(22) Filed: Sep. 10, 2008

(65) Prior Publication Data
US 2009/0018515 A1 Jan. 15, 2009

Related U.S. Application Data

(63) Continuation-in-part of application No. 11/149,744, filed on Jun. 10, 2005, now abandoned.

(51) Int. Cl.
*A61F 13/15* (2006.01)
*A61F 13/45* (2006.01)
*A61F 13/505* (2006.01)
*A61F 13/56* (2006.01)

(52) U.S. Cl.
USPC ...... 604/322; 604/346; 604/347; 604/385.01; 604/385.03; 604/391; 604/393; 604/394; 604/397; 604/400; 604/401; 604/402

(58) Field of Classification Search .................. 604/343, 604/345, 347, 358, 385.01, 385.04, 385.14, 604/385.19, 385.201, 386, 400, 385.15, 391, 604/398; 2/49.1, 49.2, 49.3, 49.4, 49.5, 48, 2/52; 433/137; 24/442; 248/690
See application file for complete search history.

(56) References Cited

U.S. PATENT DOCUMENTS

| | | | | |
|---|---|---|---|---|
| 3,618,608 | A * | 11/1971 | Brink | 604/391 |
| 5,142,743 | A * | 9/1992 | Hahn | 24/16 R |
| 5,926,926 | A * | 7/1999 | Kato | 24/442 |
| 6,911,023 | B1 * | 6/2005 | Hamilton et al. | 604/387 |
| 6,973,691 | B1 * | 12/2005 | Cordova et al. | 5/652 |
| 7,137,972 | B1 * | 11/2006 | Holberg | 604/392 |
| 2001/0044613 | A1 * | 11/2001 | Stephenson et al. | 604/385.01 |
| 2003/0135181 | A1 * | 7/2003 | Chen et al. | 604/374 |
| 2004/0111784 | A1 * | 6/2004 | Henricksen | 2/125 |
| 2005/0057080 | A1 * | 3/2005 | Collins | 297/219.12 |

* cited by examiner

*Primary Examiner* — Adam Marcetich
(74) *Attorney, Agent, or Firm* — Bruce J. Bowman

(57) ABSTRACT

A guard is provided for intercepting urine discharging from an infant such as during diaper change, bathing or clothing change. The guard is configured to attach to a changing mat or diaper without attachment to the infant and lie over the groin of the infant to receive any urine being discharged from the infant. A shield portion of the guard is configured to cover the groin of the infant while elongated ends are releasably attached to the changing mat or diaper. The guard is formed from a completely washable or disposable material. The guard includes sheathed elastic that allows the elongated ends to stretch around and over the midsection of the baby to accommodate various sizes of infants. Various completely enclosable fastening end structures with optional removability may be used to allow attachment to the changing mat or diaper, while adjustable and/or removable side pads may be provided for infant comfort.

12 Claims, 11 Drawing Sheets

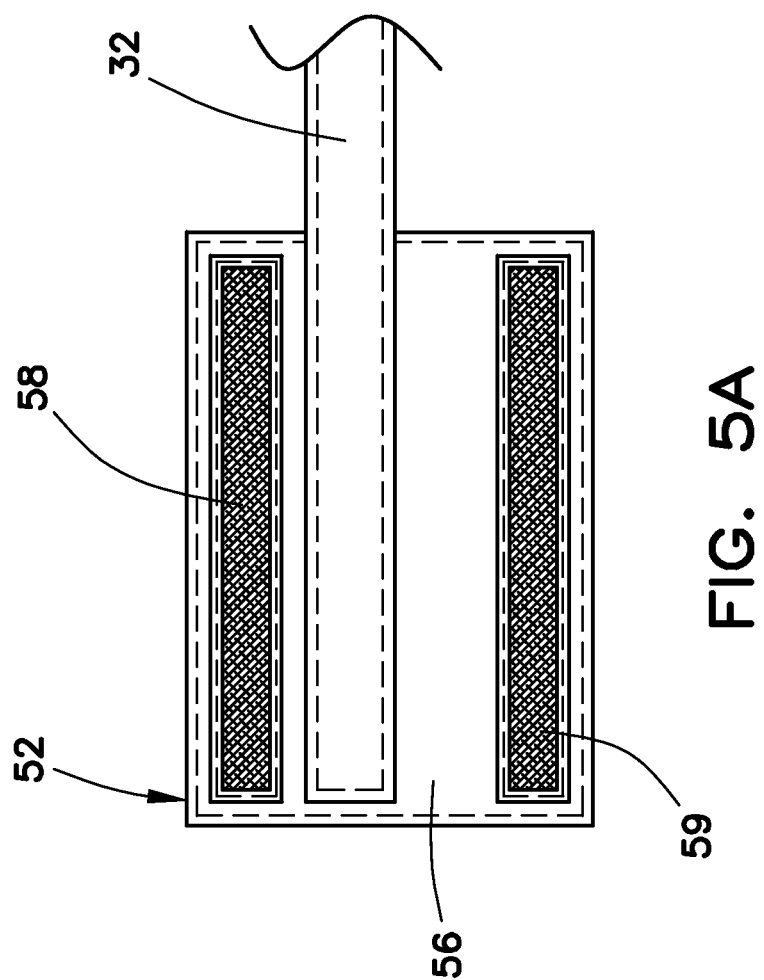

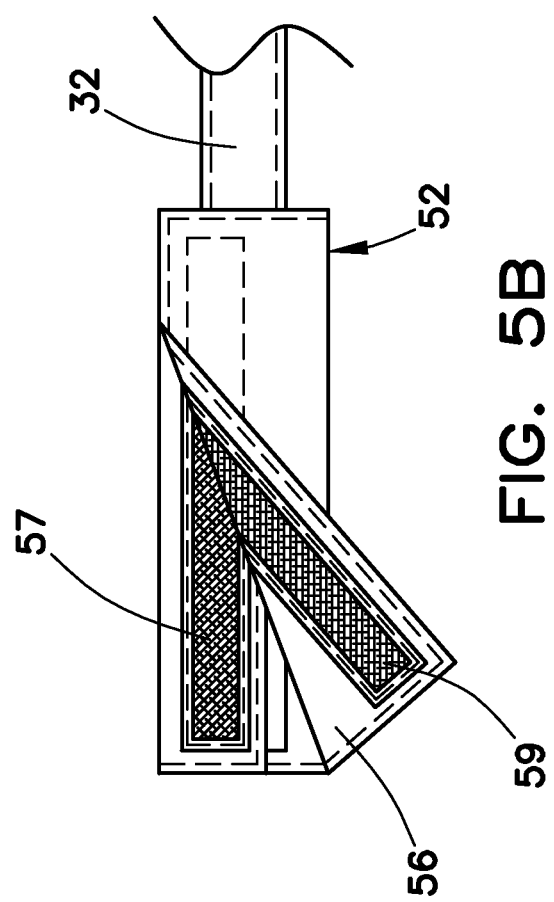

ECO-FRIENDLY URINE GUARD FOR SHIELDING AND/OR RECEIVING DISCHARGING URINE FROM AN INFANT

RELATED APPLICATIONS

This U.S. patent application is a continuation-in-part of U.S. patent application Ser. No. 11/149,744 filed Jun. 10, 2005 now abandoned entitled "Guard For Shielding and/or Receiving Discharging Urine From An Infant" the entire contents of all of which is specifically incorporated herein by this reference.

BACKGROUND OF THE INVENTION

1. Field of the Invention

The present invention relates generally to hygiene products for infants and, more particularly, to a guard for shielding and/or receiving discharging urine from an infant for protection of persons and/or objects in the vicinity of the infant during diaper change, bathing, clothing change or the like.

2. Background Information

It is well known that babies and infants lack the ability to control urination as well as other bodily functions. The inability to control urination is especially true when the infant is subject to a change in air temperature such as when a diaper or the like is being removed. Involuntary infant urination is also often caused by immersion into or removal from water such as during bathing. Moreover, involuntary urination may occur while the infant is being bathed.

When such involuntary urination occurs and the infant is without a diaper or other covering, the discharging urine can spray anywhere, haphazardly striking people and/or objects in the vicinity of the infant. This is especially true of male infants where such involuntary urination may be appropriately termed projectile urination. Because of the inherent nature of urine, it is imperative that any object, clothing or the like be immediately and thoroughly cleaned. In view of this problem, it would be desirable to stop or shield such discharging urine from reaching people, clothing, objects and/or the like.

In U.S. Pat. No. 6,379,343 issued to Stephenson et al. (hereinafter, Stephenson), the problem of shielding against involuntary urination is addressed. Particularly, in addressing this problem, Stephenson provides an infant diaper changing shield that is attachable to the infant during diaper change. The Stephenson shield utilizes an open resilient foam band in a "C" or horseshoe shape that is adapted to be resiliently clasped about the midsection of the infant. A urine receiving pad is connected to a front portion of the band. However, such a configuration is not practical for many reasons.

Particularly, because the Stephenson urine guard must be attached to the infant, infant comfort during diaper change may be compromised. Additionally, it is not conceivable how one size of foam band, no matter how resilient, can fit every size of infant; thus the need to have various sized foam bands. As the infant grows, it would therefore be necessary to acquire a new foam band. Moreover, foam is liquid permeable and not washable. This raises sanitary issues if or most likely when urine gets on the foam band. Since the foam band cannot be washed, it must be discarded and a new one purchased. While this is good for the seller, it is bad for the consumer. Still further, the shape and/or stiffness of the foam band does not lend itself to being easily stored in an infant diaper bag or the like.

Therefore, it is evident from the above that there is a need for a more practical infant urine shield.

It is further evident from the above that there is a need for an infant urine shield that is completely washable or disposable.

It is still further evident from the above that there is a need for an infant urine shield that does not compromise infant comfort.

It is even further evident from the above that there is a need for an infant urine shield wherein one size is used for all sizes of infants.

SUMMARY OF THE INVENTION

A urine guard is provided for intercepting, catching and/or receiving urine discharging from an infant such as during diaper change, bathing or clothing change of the infant. The guard is adapted to attach to a changing mat or diaper without attachment to the infant and lie over the groin thereof, and/or to lie over the infant without any attachment, to receive any urine being discharged from the infant. A shield or shield portion of the guard is configured to cover the groin of the infant while elongated ends are releasably attached to the changing mat or diaper. The guard is formed from a completely washable or disposable material.

The guard may include sheathed elastic that allows the elongated ends to stretch around and over the midsection of the baby to accommodate various sizes of infants. The shield and elongated ends are formed integral with one another. Various end structures may be used to allow attachment to the changing mat or diaper, while adjustable side pads may be provided for infant comfort. These end structures may include enclosable hook and loop type fasteners (e.g., Velcro®) that may be stationary or may be removable from the guard body. Pads or padding may be provided on and/or about the fasteners. The adjustable side pads may also be removable from the body of the urine guard as well as being adjustable along the lengths of the elongated ends of the body.

In one form of the invention, there is provided a urine guard apparatus for receiving urine discharging from an infant. The guard includes a shield formed from a liquid absorbable material and configured to cover a front groin area of the infant during use, a first elongated end integral with and extending from a first side of the shield, a second elongated end integral with and extending from a second side of the shield, a first fastener disposed on the first elongated end and adapted to releasably attach to an object on a first side of the infant, and a second fastener disposed on the second elongated end and adapted to releasably attach to the object on a second side of the infant.

In another form of the invention, there is provided a urine guard for receiving urine discharging from an infant. The guard includes a shield formed of a liquid absorbable material and configured to lie over a groin area of an infant, a first flap extending from a first side of the shield and formed of the liquid absorbable material, and a second flap extending from a second side of the shield and formed of the liquid absorbable material.

In a further form of the present invention, there is provided a completely washable or disposable, one size fits all, urine guard with stationary fasteners and removable side pads providing optional washing and/or separate washing from the urine guard thereby promoting longevity of the urine guard and its components as a whole.

In this form, the urine guard may comprise a body or shield formed from a liquid absorbable material and configured to extend over a front groin area of an infant during use; a first elongated end integral with and extending from a first upper side of the shield; the first elongated end having a length that is sufficient to reach to and extend a distance along an object under the infant; a second elongated end integral with and extending from a second upper side of the shield, the second elongated end having a length that is sufficient to reach to and extend a distance along the object under the infant; a first completely enclosable stationary fastener disposed on a back side of the first elongated end and adapted for releasable attachment to the object under the infant; and a second completely enclosable stationary fastener disposed on a back side of the second elongated end corresponding to a back side of the infant and adapted for releasable attachment to the object under the infant.

The structure of this embodiment provides a one size fits all, urine guard with stationary end fasteners and removable side pads that provide infant comfort and protection. Although the removable side pads can be adjusted in position along the length of each elongated end of the guard as desired, they can especially be adjustably positioned between the front shield portion of the guard and the stationary, completely enclosable fasteners, on each elongated end of the guard, contacting and protecting the side areas of the infant from any possible rough edges of fabric and/or fastening material on the enclosable fasteners. Because the side pads are removable completely from the guard, they allow the user the option of washing the pads. Moreover, because the side pads are positioned on each side of the front shield portion of the guard when in use, they are less likely to become soiled with urine than the shield portion.

Therefore, if only the shield portion of the guard becomes soiled, the user has the option of very simply removing the side pads and washing only the guard with the stationary completely enclosable Velcro fasteners. However, if the user desires to wash the pads, they can wash them with the guard body or separately from the guard body. Although the side pads are machine washable, due to their more delicate properties, the user may wish to wash them separately from the guard body by hand or on the delicate cycle in the washing machine or even place them in a garment bag if desired for machine washing. The removable side pads provide the added feature of optional washing and/or separate washing from the guard body, promoting longevity of the urine guard and its components as a whole which is good for the consumer.

In a yet further form of the present invention, there is provide a completely washable or disposable, one size fits all, urine guard with removable side pads, and removable, completely enclosable, hook and loop fasteners, providing optional washing and/or separate washing from the guard, promoting longevity of the guard and its components as a whole.

In this form, the urine guard may comprise a shield or body formed from a liquid absorbable material and configured to extend over a front groin area of an infant during use; a first elongated end integral with and extending from a first upper side of the shield and adapted to receive a first removable and completely enclosable hook fastener, the first elongated end having a length that is sufficient to reach to and extend a distance along an object under the infant; a second elongated end integral with and extending from a second upper side of the shield and adapted to receive a second removable and completely enclosable hook fastener, the second elongated end having a length that is sufficient to reach to and extend a distance along the object under the infant; a first removable and completely enclosable, hook fastener disposed on a back side of the first elongated end and adapted for releasable attachment to the object under the infant; and a second removable and completely enclosable, hook fastener disposed on a back side of the second elongated end corresponding to a back side of the infant and adapted for releasable attachment to the object under the infant.

The structure of this embodiment provides a one size fits all urine guard with removable side pads that provide infant comfort and protection. Although, the removable side pads can be adjusted in position along the length of each elongated end of the guard as desired, they can especially be adjustably positioned between the front shield portion of the guard and the removable completely enclosable fasteners on each elongated end of the guard contacting and protecting the side areas of the infant from any possible rough edges of fabric and/or Velcro on the completely enclosable fasteners. Because the pads are removable they allow the user the option of washing the pads. Likewise, the removable hook and loop style enclosures allow the user the option of washing the completely enclosable hook and loop style fasteners.

Because the side pads and completely enclosable hook and loop style fasteners are positioned to each side of the front shield portion of the guard when in use, all four separate removable pieces are less likely to become soiled with urine than the shield portion. Therefore, if only the shield portion of the guard becomes soiled, the user has the option of very simply removing the side pads and enclosable hook and loop fasteners and washing only the guard body.

Moreover, in this embodiment of the urine guard, the elongated ends of the guard are affixed with loop style fasteners to receive the completely enclosable hook style fasteners. Therefore, if only the guard body is washed (without the side pads and enclosable hook and loop fasteners) the loop fastener affixed to each of the elongated ends of the guard will not adhere to other articles of clothing in the wash. If the user desires to wash the side pads and/or enclosable hook and loop fasteners, they can wash them with the guard or separately from the guard body. The enclosable fasteners are made of a durable material capable of withstanding regular washing preferably in the closed position. Although the pads are machine washable, due to their more delicate properties, the user may wish to wash the pads separately from the guard body by hand or on the delicate cycle in the washing machine or even place them in a garment bag if desired for machine washing. The removable side pads and removable enclosable hook and loop style fasteners provide the added feature of optional washing and/or separate washing from the guard body, promoting longevity of the guard and its components as a whole which is good for the consumer.

In a still further form of the present invention, there is provided a completely washable or disposable, one size fits all, urine guard, with removable and completely enclosable, padded hook and loop style fasteners, providing optional washing and/or separate washing from the guard body promoting longevity of the guard and its components as a whole.

In this form, the urine guard may comprise a shield or body formed from a liquid absorbable material and configured to extend over a front groin area of an infant during use; a first elongated end integral with and extending from a first upper side of the body and adapted to receive a first removable and completely enclosable padded hook fastener, the first elongated end having a length that is sufficient to reach to and extend a distance along an object under the infant; a second elongated end integral with and extending from a second side of the shield adapted to receive a second removable and completely enclosable padded hook fastener, the second elongated end having a length that is sufficient to reach to and extend a distance along the object under the infant; a first removable and completely enclosable, padded, hook fastener disposed on a back side of the first elongated end and adapted for releasable attachment to the object under the infant; and a second removable and completely enclosable, padded, hook fastener disposed on a back side of the second elongated end corresponding to a back side of the infant and adapted for releasable attachment to the object under the infant.

The structure of this embodiment provides a one size fits all urine guard with removable completely enclosable, padded hook and loop style fasteners. The removable padded completely enclosable hook and loop style fasteners are adjustable in position along the length of each elongated end of the guard. Because the pads are attached to the entire horizontal end of each completely enclosable fastener, they serve to contact and protect the side areas of the infant from any possible rough edges of fabric and/or hook and loop material on the enclosable fasteners. Because the padded completely enclosable fasteners are removable they allow the user the option of washing them. Because the padded enclosable Velcro fasteners are positioned to each side of the shield portion of the guard, when in use, they are less likely to become soiled with urine than the shield portion.

Therefore, if only the shield portion of the guard becomes soiled, the user has the option of very simply removing the padded enclosable hook and loop style fasteners and washing only the guard. In this embodiment, the elongated ends of the guard are affixed with loop fastener to receive the padded enclosable hook fastener. Therefore, if only the guard body is washed (without the padded enclosable hook and loop style fasteners) the loop fastener affixed to the elongated ends of the guard will not adhere to other articles of clothing in the wash. If the user desires to wash the padded enclosable hook and loop style fasteners, they can wash them with the guard body or separately from the guard body. The padded enclosable fasteners are made of a durable material capable of withstanding regular washing preferably in the closed position. However, due to the delicate properties of the pad portion of the completely enclosable fasteners, the user may wish to wash the padded enclosable fasteners separate from the guard body by hand or on the delicate cycle in the washing machine or even place them in a garment bag if desired for machine washing. The removable padded completely enclosable hook and loop fasteners provide the added feature of optional washing and/or separate washing from the guard, promoting longevity of the guard and its components as a whole which is good for the consumer.

In a yet further form of the present invention, there is provided a completely washable or disposable one size fits all, bath time urine guard, with side ballasts configured to adhere to the sides of an infant when wet for stabilizing the shield on the infant.

In this form, the urine guard may comprise a shield formed of a liquid absorbable material and configured to lie over a groin area of an infant, a first ballast extending from a first middle lateral side of the shield and formed of the liquid absorbable material, the first ballast configured to adhere to sides of the infant when wet for stabilizing the shield on the infant, and a second ballast extending from a second middle lateral side of the shield and formed of the liquid absorbable material, the second ballast configured to adhere to sides of the infant when wet for stabilizing the shield on the infant.

The structure of this embodiment provides a one size fits all, urine guard for use during a bath with sides (ballasts) that are configured to provide stability to the guard when wet by adhering to the sides of the infant. The guard body is formed of a soft absorbent material that is safe and effective to use to wash an infant during a bath. The side cloth ballasts can be used in conjunction with the shield portion of the guard for safely washing the groin area as well as other areas. The softness, shape, position, width and length are such as to allow comfortable washing of various areas of the infant.

Also provided is a bib version of the bath time urine guard. In addition to side ballasts, the bib version has first and second bib portions that extend from respective first and second upper sides of the shield portion of the guard. The additional material of the bib version provides warmth and comfort to an infant during the bath. The side ballasts provide simultaneous stability to hold the urine guard in place during the bath. The side ballasts are formed of the same soft liquid absorbable material that is safe and effective to use to wash the infant during a bath. When used dry, the material is such as to provide effective drying of the infant immediately after a bath.

There is also provided a method of intercepting urine discharging from an infant during diaper change. The method includes the steps of (a) placing a clean diaper under a soiled diaper of an infant, (b) placing a urine guard as described herein, (c) attaching the first and second end structures of the urine guard to the object, (d) removing the soiled diaper, (e) readying the clean diaper to be attached to the infant, (f) removing the urine guard, and (g) securing the clean diaper to the infant.

The present urine shield is completely or can be partially washable or disposable, does not compromise infant comfort since nothing attaches to the infant, and one size is used for all sizes of infants since the present urine shield is fully adjustable.

In all of the above forms of the present urine guard, it should be appreciated that the washable, liquid absorbable material for the various parts may be formed, entirely, partially or substantially of an eco-friendly and/or easily renewable material such as bamboo, hemp or the like. Various parts or all of the guard may be made disposable through eco-friendly, non-cloth, biodegradable materials that provide economic feasibility and environmentally friendly responsibility which may also be environmentally beneficial to dispose of after one use or soiling. This would find use in hospital and daycare settings. The material could therefore contain a composition that is beneficial to the environment and/or helps aid in decomposition such as, but not limited to, a plant based material or food based material (e.g. cornstarch). The materials may include nutrients and/or components that are biodegradable and beneficial to the soil (e.g. fluffed wood pulp and viscose rayon). Sodium polyacrylate crystals (known as "super absorbent polymer" or SAP) are another option available to form the current urine guard. Because of the absorbent properties of SAP, these crystals can be added to compost and biosolids to increase moisture retention and enrich soil. Biodegradable natural and recycled polymers may also be used.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 5A is an enlarged view an end structure of the urine guard of FIG. 4 in an open position;

FIG. 5B is an enlarged view of the end structure of the urine guard of FIG. 4 in a partially closed position;

Like reference numerals indicate the same or similar parts throughout the several figures.

DETAILED DESCRIPTION OF THE PREFERRED EMBODIMENTS

Figure 1:
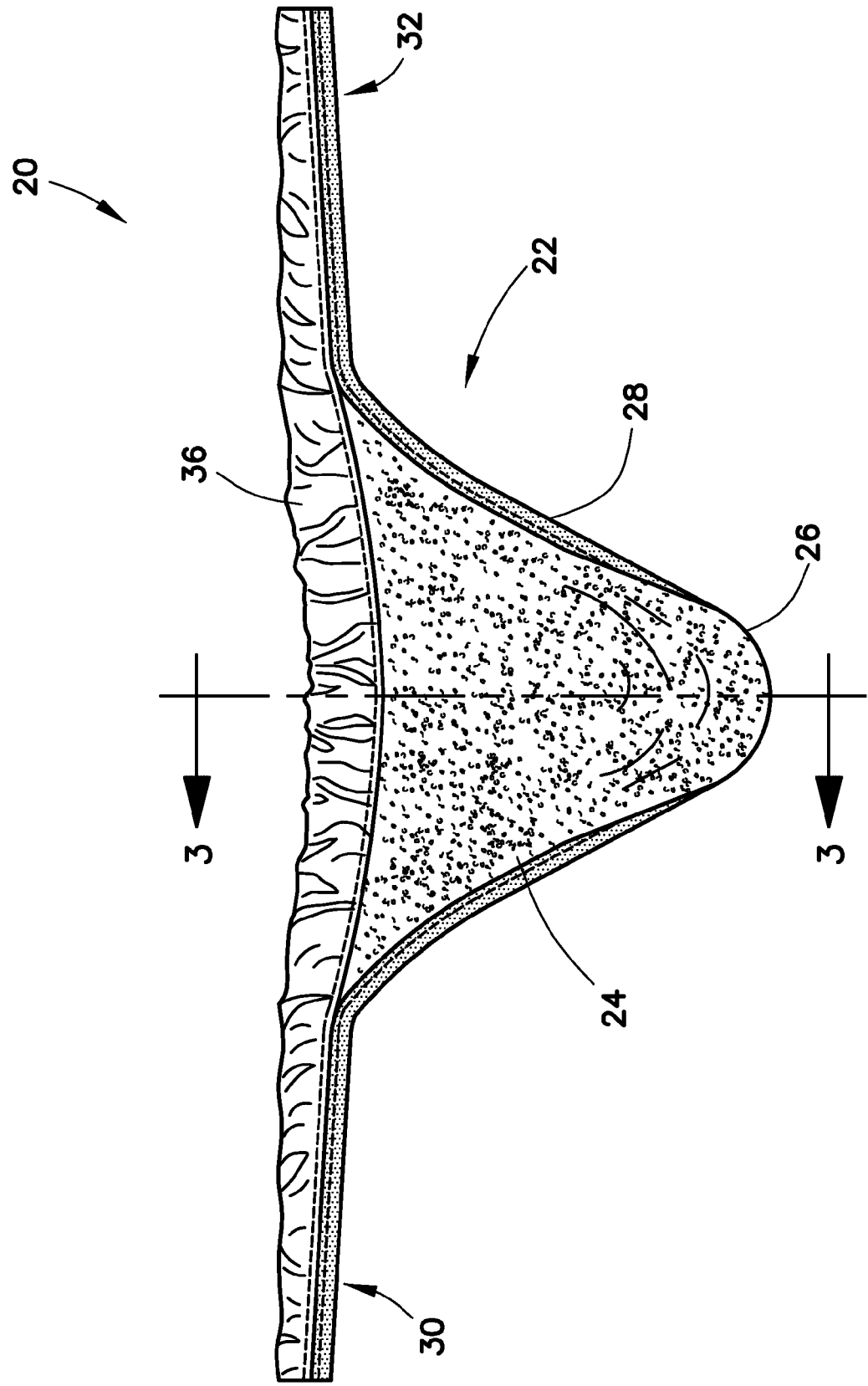
FIG. 1 is a top view of an embodiment of a urine guard in accordance with the present principles.
Figure 2:
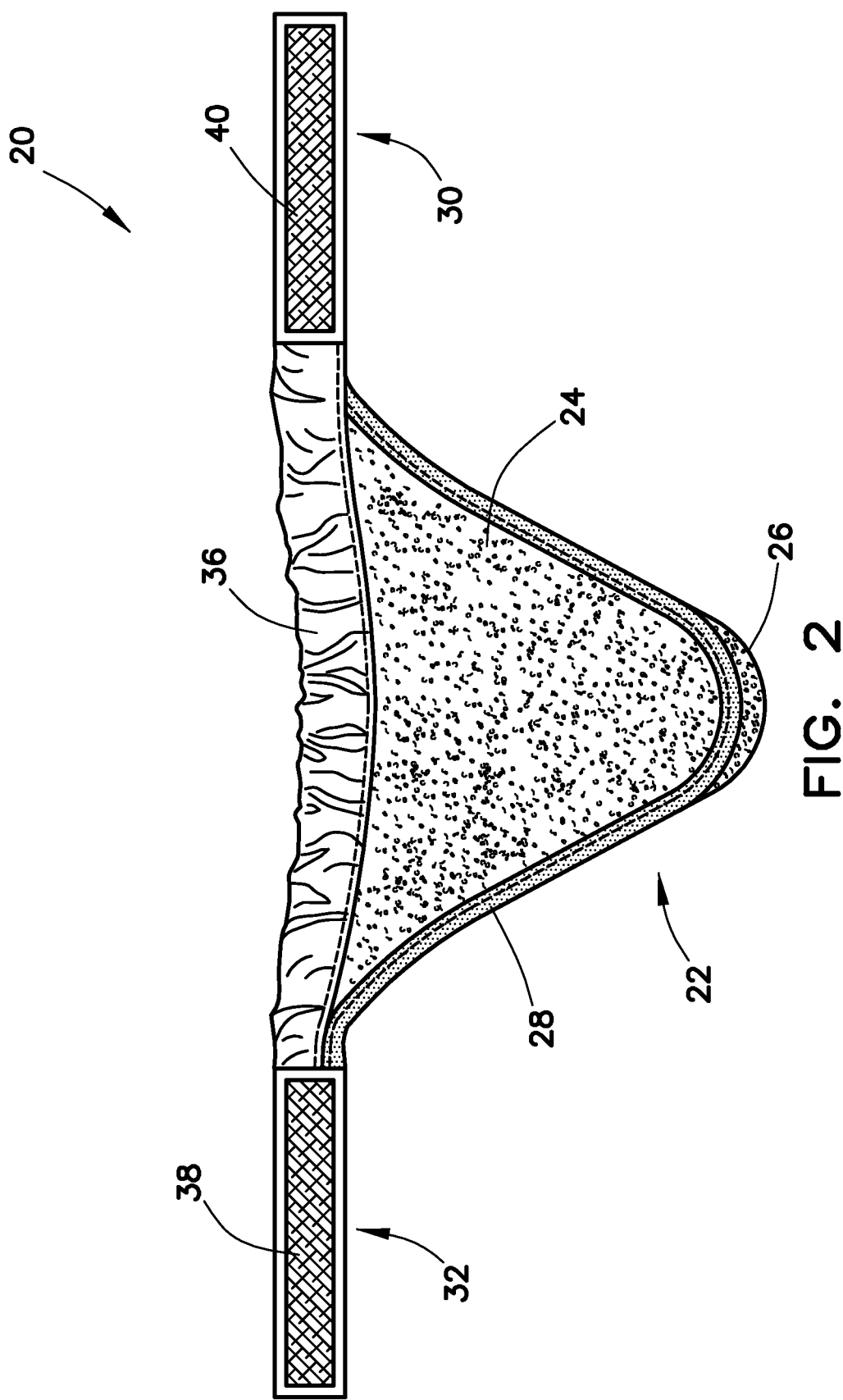
FIG. 2 is a rear view of the urine guard of FIG. 1.
Figure 3:
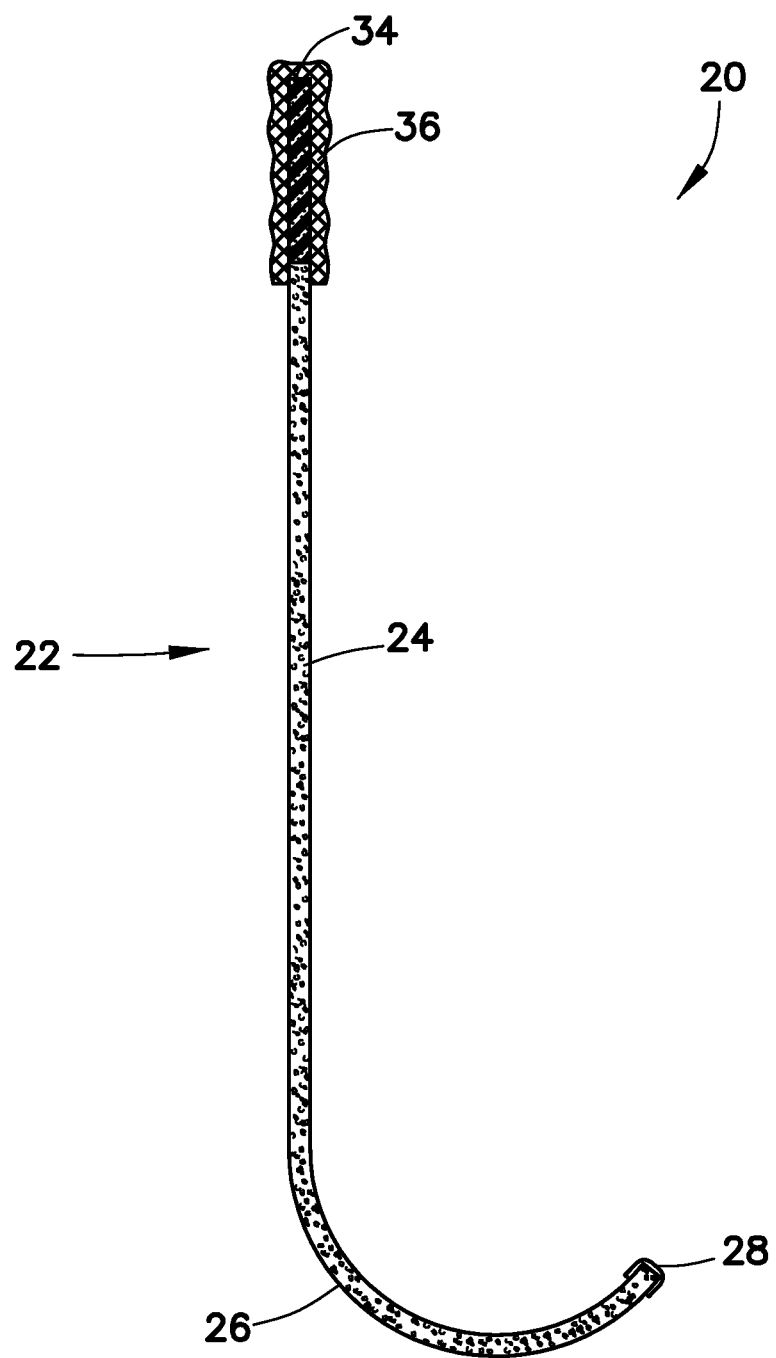
FIG. 3 is a sectional view of the urine guard of FIG. 1 taken along line 3-3 thereof.

Referring to FIGS. 1-3, there is depicted a front view (FIG. 1), a rear view (FIG. 2) and a sectional view (FIG. 3) of an embodiment of a guard or shield, generally designated 20, for catching, receiving and/or absorbing urine discharging from a baby such as during changing of the baby's diaper. The guard 20 has a unitary body 22 formed of a soft, pliable, liquid-absorbent material that may be a natural fiber such as cotton or the like, a man-made fiber or a combination of natural and man-made fibers. The body 22 may be a single layer of material or may be two or more (multiple) layers of material. In a washable (and this re-usable) form, the body 22 may be formed of terry-cloth. In a disposable form, the body 22 may be formed of a disposable-type diaper material such as is known in the art.

The various parts may also be made from different materials depending on use. For example, the body 22 may be made from a more highly washable material than the side pads 66 and 68 since the body 22 will probably need to be washed more often than the side pads 66, 68. It should be appreciated that the washable, liquid absorbable material for the various parts may be formed, entirely, partially or substantially of an eco-friendly and/or easily renewable material such as bamboo, hemp or the like. Bamboo for instance, has four (4) times more absorbency than cotton, is naturally anti-fungal and antimicrobial, and can be Mercerized for extra strength and long life.

It should also be appreciated that the various parts may be made in a disposable version. Eco-friendly, non-cloth, biodegradable materials are used for this purpose. In this manner, it would be economically feasible and environmentally responsible or friendly and could be environmentally beneficial to dispose of the disposable urine guard after one use or soiling. This would find use in hospital and daycare settings. Waste methods could include but not be limited to landfills, composting or flushing down a toilet. The material could therefore contain a composition that is beneficial to the environment and/or helps aid in decomposition such as, but not limited to, a plant based material or food based material (e.g. cornstarch). The materials may include nutrients and/or components that are biodegradable and beneficial to the soil (e.g. fluffed wood pulp and viscose rayon, both of which are harvested from trees under the Sustainable Forestry Initiative established in 1994).

Sodium polyacrylate crystals (known as "super absorbent polymer" or SAP) are another option available to form the current urine guard such as are used in disposable diapers, and which can hold one hundred times their weight in water. Because of the absorbent properties of SAP, these crystals can be added to compost and biosolids to increase moisture retention and enrich soil. Biodegradable natural and recycled polymers may also be used.

The body 22 has an apron or shield 24 in the general shape of a triangle or the groin area of an infant. A cup 26 is formed at the end of the shield 24. The cup 26 extends rearwardly to provide coverage below the groin area. A first elongated end 30 extends from an upper left (as viewed in FIG. 1) top area of the shield 24, while a second elongated end 32 extends from an upper right (as viewed in FIG. 1) top area of the shield 24. An elastic band 34 (see FIG. 3) is provided along the top end of the body 22 from the end of the first elongated end 30 to the second elongated end 32. A sheath 36 covers the elastic band 34. The sheath 36 is preferably, but not necessarily, formed of a smooth, satin or satin-like material.

As seen in FIG. 2, a fastening or fastener portion 38 preferably, but not necessarily, formed from a hook material of a hook and loop type fastening system (e.g. Velcro®) is situated on the rear side of the elongated end 32. The fastening portion 38 extends a length of the elongated end 32. Likewise, a fastening or fastener portion 40 preferably, but not necessarily, formed from a hook material of a hook and loop type fastening system (e.g. Velcro®) is situated on the rear side of the elongated end 30. The fastening portion 40 extends a length of the elongated end 30. Each fastening portion 38, 40 is adapted to releasably attach its respective elongated end 32, 30 to a changing mat disposed beneath the infant during diaper change or, alternatively, to a new diaper positioned underneath a soiled diaper (i.e. a diaper to be changed). In this manner, the upper portion of the body 22, particularly the sheath 36 covered elastic 34, is stretched over the midsection of the baby. This allows the shield 24 to lie over the groin area of the baby, with the cup 26 extending downward around the infant's genitals.

The guard 20 is shown in FIGS. 1-3 in an un-stretched or relaxed state wherein the sheath 36 is at least somewhat bunched together. This allows the sheath 36, and thus the upper body 22, to stretch along with the elastic 34 to accommodate the use of the guard with any size of infant. In this manner, one guard 20 fits all.

Figure 4:
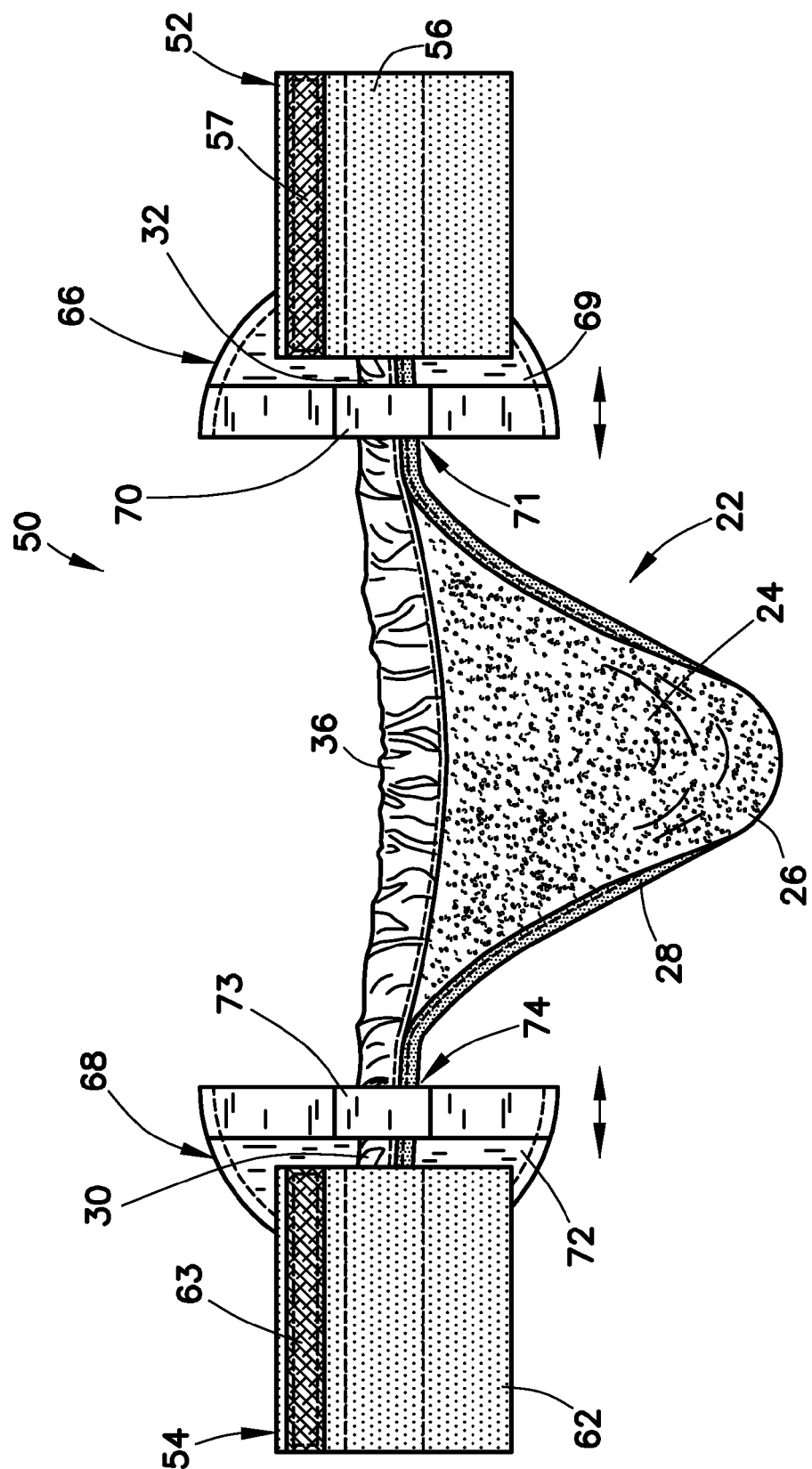
FIG. 4 is a top view of another embodiment of a urine guard in accordance with the present principles.

Referring now to FIG. 4, there is depicted another embodiment of a urine guard, generally designated 50. The guard 50 is a modification of the guard 20 shown in FIGS. 1-3 and thus includes the features and function(s) thereof described with regard to guard 20 whose reference numbers are the same as depicted on the urine guard 50. The guard 50, however, does not include the fastener portions 38 and 40 on the respective elongated ends 32 and 30. Rather, the guard 50 includes a first end structure 52 disposed on elongated end 32 and a second end structure 54 disposed on elongated end 30. The first and second end structures 52, 54 are adapted to releasably attach or fix the guard 50 (i.e. elongated ends 30, 32) to the changing mat or diaper, as well as cover and/or completely enclose the fastening portions (described below) thereof for washing of the guard 50 in order that the fastening portions do not accumulate foreign material or damage other articles of clothing in the wash as such fastening portions are susceptible of doing.

The first end structure 52 is formed of a body of material 56 that is sewn or otherwise fixedly attached to the elongated end 32. A first fastening portion 57 preferably, but not necessarily, formed from a loop material of a hook and loop type fastening system (e.g. Velcro®), is disposed on an upper outside (front) portion of the material 56 of the first end structure 52. Referring additionally to FIG. 5A, the first end structure 52 includes a second fastening portion 58 preferably, but not necessarily, formed from a hook material of a hook and loop type fastening system (e.g. Velcro®), that is disposed on an upper inside (rear) portion of the material 56, while a third fastening portion 59 preferably, but not necessarily, formed from a hook material of a hook and loop type fastening system (e.g. Velcro®) is disposed on a lower inside (rear) portion of the material 56.

The second and third fastening portions 58 and 59 allow the first end structure 52 to be releasably attached to a changing mat under the infant or a new diaper under the infant. The first fastening portion 57 is used to fold up the first end structure 52 for washing of the guard 50. Referring to FIG. 5B, the first end structure 52 is shown in a partially folded state. The upper portion of the material 56 is first folded downward and rearward such that the first fastening portion 57 faces the rearward direction. This situates the second fastening portion 58 next to the elongated end 32 and eventually within the folded end structure 52. Next, the lower portion of the material 56 is folded upward and forward such that the third fastening portion 59 attaches to the first fastening portion 57.

Referring back to FIG. 4, the second end structure 54 is fashioned in like manner to the first end structure 52. Thus, the second end structure 54 is formed of a body of material 62 that is sewn or otherwise fixedly attached to the elongated end 30. A first fastening portion 63 preferably, but not necessarily, formed from a loop material of a hook and loop type fastening system (e.g. Velcro®), is disposed on an upper outside (front) portion of the material 62 of the second end structure 54. While not shown, the second end structure 54 includes a second fastening portion preferably, but not necessarily, formed from a hook material of a hook and loop type fastening system (e.g. Velcro®), that is disposed on an upper inside (rear) portion of the material 62, and a third fastening portion preferably, but not necessarily, formed from a hook material of a hook and loop type fastening system (e.g. Velcro®) is disposed on a lower inside (rear) portion of the material 62. The second end structure 54 folds in like manner to the first end structure 52.

The guard 50 also includes a first side pad 66 disposed on the elongated end 32 and a second side pad 68 disposed on the elongated end 30. The first side pad 66 is formed by a body 69 of a washable soft, preferably but not necessarily, padded material. The second side pad 68 is formed by a body 72 of a washable soft, preferably but not necessarily padded material. The body 69 of the first side pad 66 is shaped to abut and fit the contours of a side of the infant when the guard 20 is in place. Likewise, the body 72 of the second side pad 68 is shaped to abut and fit the contours of the other side of the infant when the guard 20 is in place. As such, each body 69, 72 is depicted as a generally half-circle shape. Of course, other shapes may be used.

The first side pad 66 includes a band 70 that forms an opening 71 through which extends the elongated end 32. As represented by the double-headed arrow immediately below the body 69, position of the first side pad 66 relative to the elongated end 32 is adjustable. This allows the user to properly position the first side pad 66 relative to the side of the infant for use. More particularly, the first side pad 66 is positionable between the shield 24 and the end structure 52. It should be appreciated that the adjustment length between the end structure 52 and the shield 24 may be longer than that shown. This may be accomplished by elongating the elongated end 32 and/or shortening the longitudinal length of the end structure 52 adjacent the first side pad 66.

Likewise, the second side pad 68 includes a band 73 that forms an opening 74 through which extends the elongated end 30. As represented by the double-headed arrow immediately below the body 72, position of the second side pad 68 relative to the elongated end 30 is adjustable. This allows the user to properly position the first side pad 68 relative to the side of the infant for use. More particularly, the second side pad 68 is positionable between the shield 24 and the end structure 54. It should be appreciated that the adjustment length between the end structure 54 and the shield 24 may be longer than that shown. This may be accomplished by elongating the elongated end 30 and/or shortening the longitudinal length of the end structure 54 adjacent the second side pad 68.

The first side pad 66 may be removable from the elongated end 32 in addition to being movable along the length of the elongated end 32. Likewise, the second side pad 68 may be removable from the elongated end 30 in addition to being movable along the length of the elongated end 30. This allows separate washing of the side pads 66, 68 from the guard body or shield. As such, the side pads 66, 68 may be referred to as removable side pads 66, 68.

Figure 6:
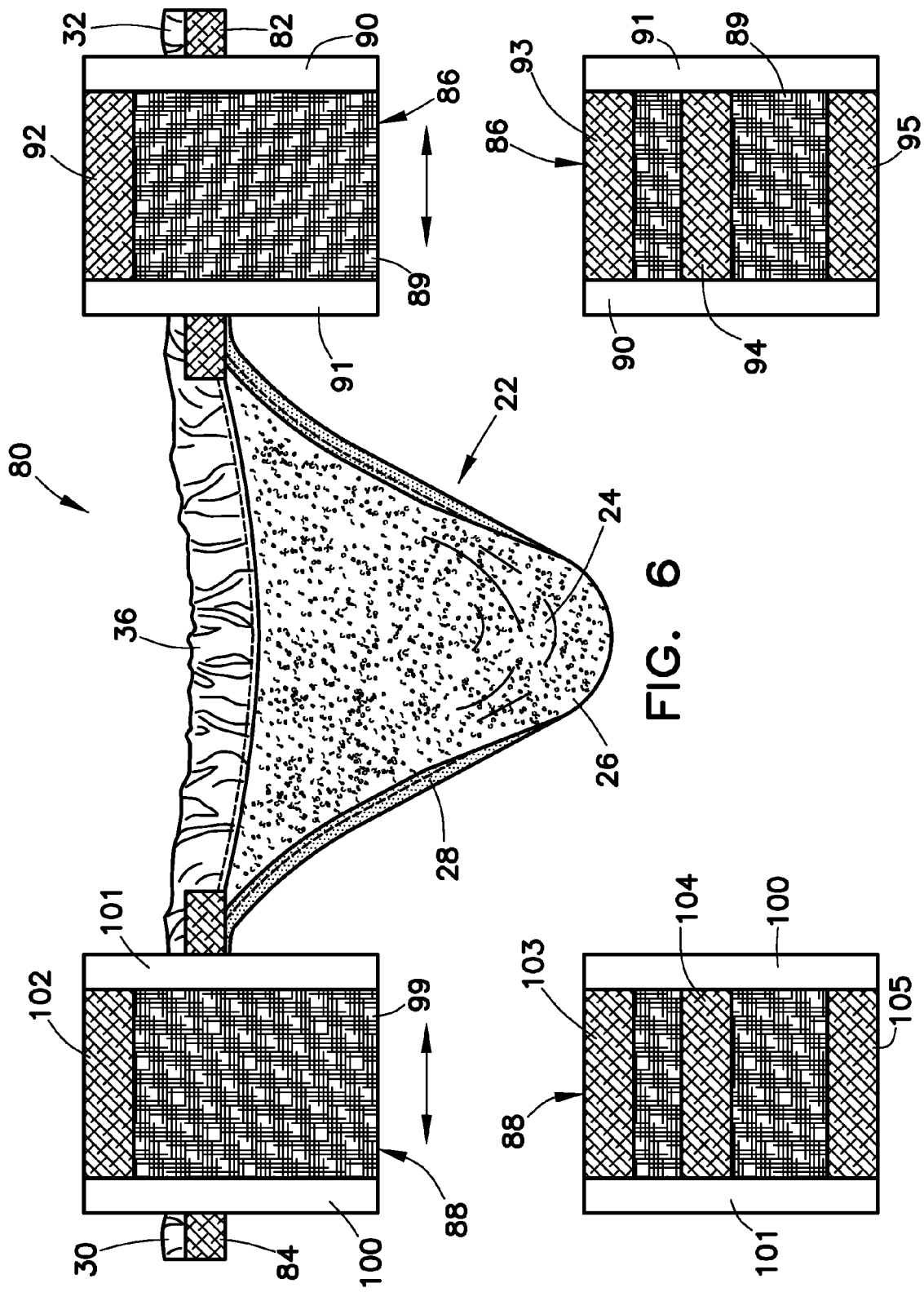
FIG. 6 is a top view of another embodiment of a urine guard in accordance with the present principles, the end structure thereof also shown in rear view.

Referring now to FIG. 6, there is depicted another embodiment of a urine guard generally designated 80. The guard 80 is a modification of the guards 20 and 50 shown in FIGS. 1-3 and FIG. 4 and thus includes the features and function(s) thereof described with regard to guards 20 and/or 50 whose reference numbers are the same as depicted on the urine guard 80. The guard 80, however, includes adjustable end structures. Particularly, the elongated end 32 has a strip 82 of fastening material that is preferably, but not necessarily, formed from a loop material of a hook and loop type fastening system (e.g. Velcro®). The strip 82 preferably extends the length of the elongated end 32. Likewise, the elongated end 30 has a strip 84 of fastening material that is preferably, but not necessarily, formed from a loop material of a hook and loop type fastening system (e.g. Velcro®). The strip 84 preferably extends the length of the elongated end 30.

The guard 80 includes a first end structure 86 that is removably situated on the elongated end 32. As such, the first end structure 86 may be adjustably positioned anywhere along the elongated end 32 as represented by the double-headed arrow depicted below the first end structure 86. Likewise, the guard includes a second end structure 88 that is removably situated on the elongated end 30. As such, the second end structure 88 may be adjustably positioned anywhere along the elongated end 30 as represented by the double-headed arrow depicted below the first end structure 88.

The first end structure 86 is characterized by a portion of material 89 having a first side pad 90 and a second side pad 91. A first fastening portion 92 is disposed on an outer upper portion of the material 89 between the pads 90, 91. The first fastening portion 92 is preferably, but not necessarily, formed from a loop material of a hook and loop type fastening system (e.g. Velcro®). Shown below the first end structure 86 is a reverse or rear view of the first end structure 86. The rear side of the first end structure 86 has a second fastening portion 93 preferably, but not necessarily, formed from a hook material of a hook and loop type fastening system (e.g. Velcro®), that is disposed on an upper portion of the material 89. The rear side of the first end structure 86 also includes a third fastening portion 94 preferably, but not necessarily, formed from a hook material of a hook and loop type fastening system (e.g. Velcro®) opposite to that of the strip 82 for releasable attachment (and therefore adjustability) of the first end structure 86 relative to the elongated end 32. Furthermore, the rear side of the first end structure 86 has a fourth fastening structure 95 preferably, but not necessarily, formed from a hook material of a hook and loop type fastening system (e.g. Velcro®) disposed on a lower portion of the material 89.

The second and fourth fastening portions 93 and 95 allow the first end structure 86 to be releasably attached to a changing mat under the infant or a new diaper under the infant. The first fastening portion 92 along with the fourth fastening portion 95 is used to fold up and completely enclose the first end structure 86 for washing of the guard 80 in like manner to the end structures of the guard 50.

In like manner as the first end structure 86, the second end structure 88 is characterized by a portion of material 99 having a first side pad 100 and a second side pad 101. A first fastening portion 102 is disposed on an outer upper portion of the material 99 between the pads 100, 101. The first fastening portion 102 is preferably, but not necessarily, formed from a loop material of a hook and loop type fastening system (e.g. Velcro®). Shown below the second end structure 88 is a reverse or rear view of the second end structure 88. The rear side of the second end structure 88 has a second fastening portion 103 preferably, but not necessarily, formed from a hook material of a hook and loop type fastening system (e.g. Velcro®), that is disposed on an upper portion of the material 99. The rear side of the second end structure 88 also includes a third fastening portion 104 preferably, but not necessarily, formed from a hook material of a hook and loop type fastening system (e.g. Velcro®) opposite to that of the strip 84 for releasable attachment (and therefore adjustability) of the second end structure 88 relative to the elongated end 30. Furthermore, the rear side of the second end structure 88 has a fourth fastening structure 105 preferably, but not necessarily, formed from a hook material of a hook and loop type fastening system (e.g. Velcro®) disposed on a lower portion of the material 99.

The second and fourth fastening portions 103 and 105 allow the second end structure 88 to be releasably attached to a changing mat under the infant or a new diaper under the infant. The first fastening portion 102 along with the fourth fastening portion 105 is used to fold up and completely enclose the second end structure 88 for washing of the guard 80 in like manner to the end structures of the guard 50.

The pads 90 and 91 of the end structure 86 and the pads 100 and 101 of the end structure 88 provide comfort to the infant during use of the guard 80. This is particularly true no matter how the guard is attached or how the infant moves during use. The pads 90, 91, 100, 101, in another sense, also protect the infant from the edges of the fabric constituting the end structures 86, 88.

Figure 7:
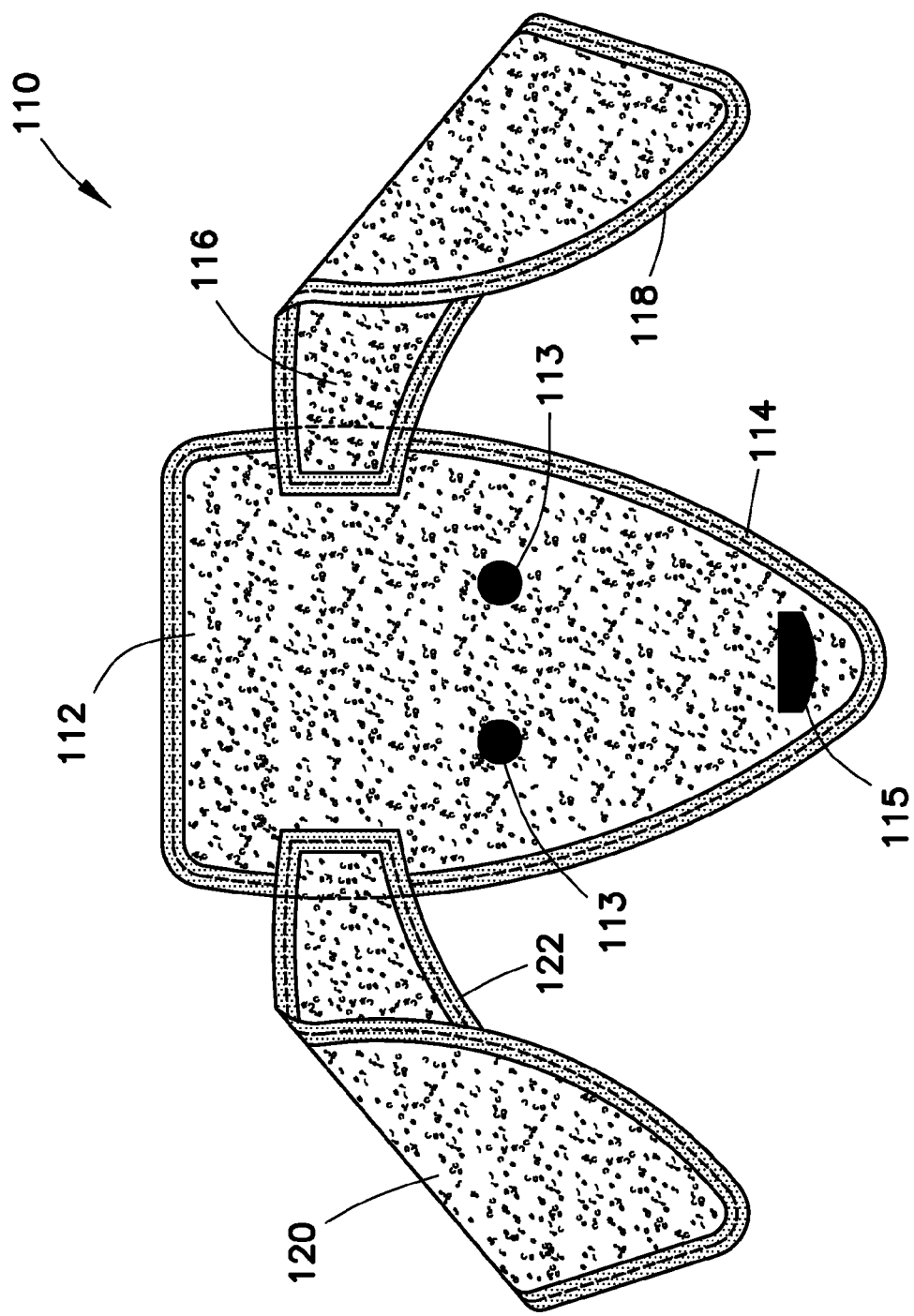
FIG. 7 is a top view of a further embodiment of a urine guard in accordance with the present principles.

Referring to FIG. 7, there is depicted an embodiment of a urine guard, generally designated 110, fashioned for use when bathing an infant. The guard 110 is formed of a generally shield-shaped body 112 fashioned from a soft, pliable, liquid-absorbent material that may be a natural fiber such as cotton or the like, a man-made fiber or a combination of natural and man-made fibers. Other materials may be used as discussed below. The body or shield 22 may be a single layer of material or may be two or more (multiple) layers of material. In a washable (and this re-usable) form, the shield 22 may be formed of terry-cloth. In a disposable form, the shield 22 may be formed of a disposable-type wash-cloth material such as is known in the art.

The shield 112 is particularly shaped to cover and/or lie over the groin area of an infant particularly when the infant is in the bath. Cording 114 is provided around the shield 112. The shield 112 further includes first and second flaps or ballasts 116, 120 each one of which extends from an upper side of the shield 112. The ballasts 116, 120 are preferably, but not necessarily, fashioned from the same material as the body 112. Ballast 116 preferably, but not necessarily, includes cording 118 on the perimeter thereof. Likewise, ballast 120 preferably, but not necessarily, includes cording 122 on the perimeter thereof. Moreover, the ballasts 116, 120 may be sized to fold over and reach the end of the shield 112. The ballasts may be longer if desired. This allows the ballasts 116, 120 to be used to wash various parts of the infant while the shield 112 remains over the groin area for receiving and absorbing projectile urine discharge. As a novelty, since the shield 112 and ballasts 116 and 120 resemble the face of a dog or other animal, the shield 112 may include eyes 113 and a nose 115. The ballasts 116, 120 further provide stability to the urine guard when wet (i.e. when being used during bathing of an infant). By draping or lying across sides of the infant, the ballasts serve as stabilizers for the guard to keep the urine guard on the infant.

Figure 8:
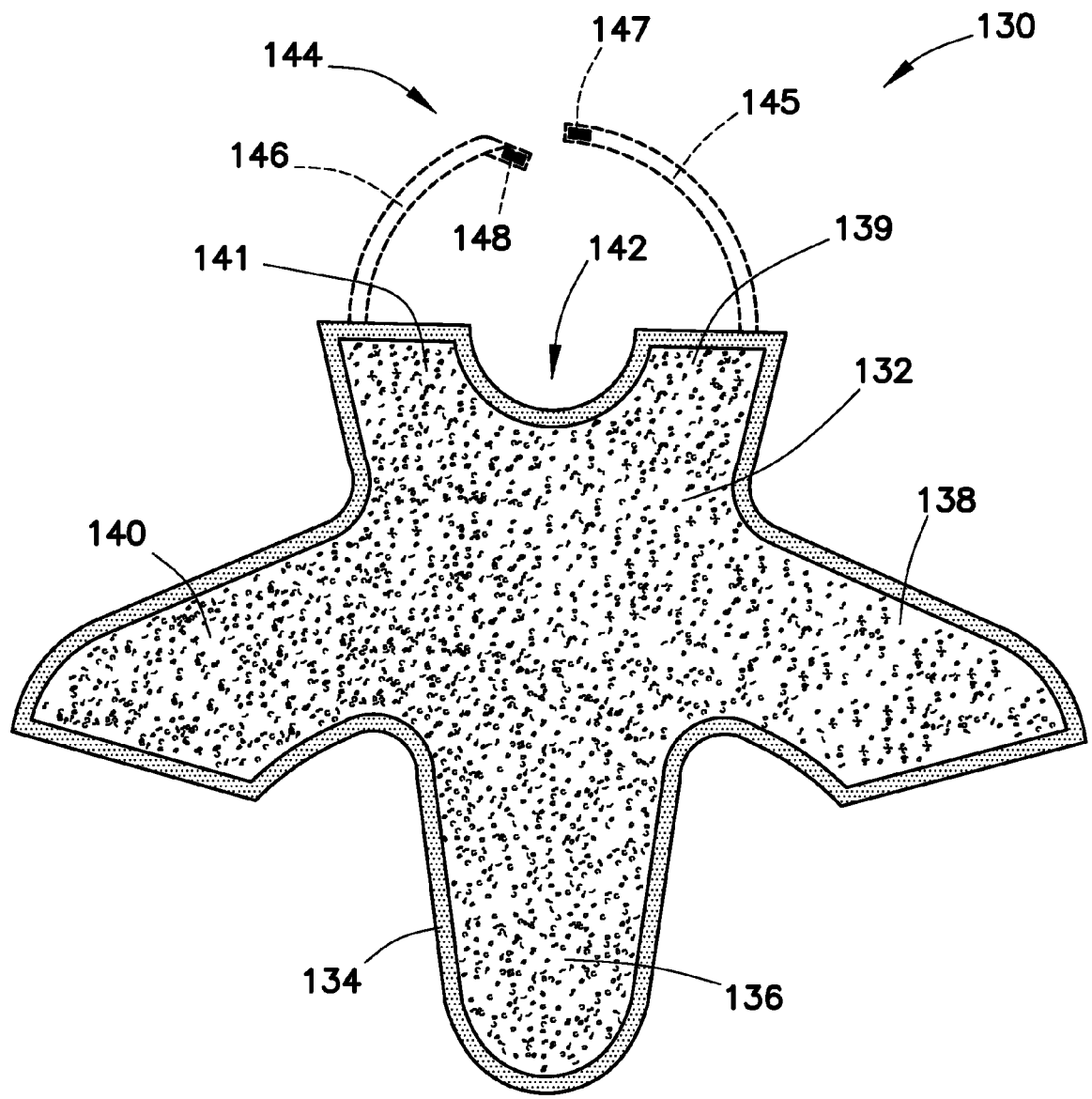
FIG. 8 is a top view of a yet another embodiment of a urine guard in accordance with the present principles.

Referring to FIG. 8, there is depicted an embodiment of a urine guard, generally designated 130, fashioned as a bib or the like that may be used during bathing of the infant or otherwise. The guard 130 has a body or shield 132 formed from a soft, pliable, liquid-absorbent material that may be a natural fiber such as cotton or the like, a man-made fiber or a combination of natural and man-made fibers. The body 132 may be a single layer of material or may be two or more (multiple) layers of material. In a washable (and this re-usable) form, the body 132 may be formed of terry-cloth. In a disposable form, the body 132 may be formed of a disposable-type wash-cloth material such as is known in the art. Cording 134 is provided on the perimeter of the body 132.

The body 132 has a lower appendage 136 that is shaped to cover the groin or groin area of an infant. A first ballast 138 extends from one side of the body 132, while a second ballast 140 extends from another side of the body 132 opposite to that of the first ballast 138. Each ballast 138, 140 preferably, but not necessarily, has the same shape. The ballasts 138 and 140 stabilize the guard when placed over an infant in like manner to the version above and in other manners as well. The body 132 further defines a neck cutout 142 formed between two upper portions 139, 141. The upper portions 139, 141 are configured to lie on/over the shoulders of the infant.

Shown in phantom (dashed lines) is an optional guard retaining means 144 configured to keep the guard 130 in a proper position on the infant. Particularly, the retaining means 144 has a first strap 145 extending from the upper portion 139, and a second strap 146 extending from the upper portion 141. The first strap 145 has a portion 147 of one of a hook or loop material of a hook and loop type fastener (e.g. Velcro®) on an end thereof, while the second strap 146 has a portion 148 of a hook or loop material of a hook and loop type fastener (e.g. Velcro®) opposite to that of fastener portion 147. In this manner, the straps 145, 146 may be releasably attached around and behind the neck of the infant.

Figure 9:
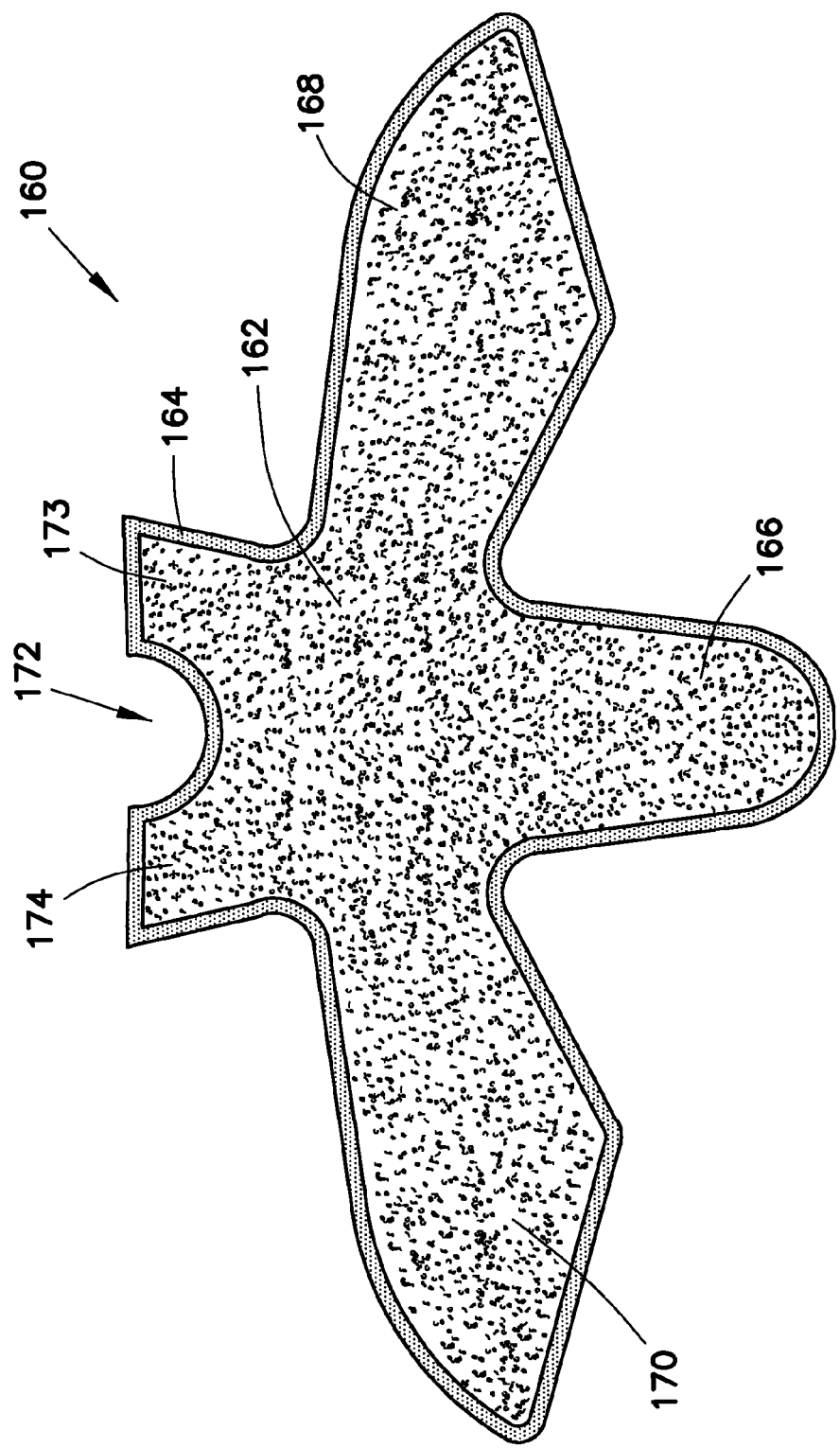
FIG. 9 is a top view of a still further embodiment of a urine guard in accordance with the present principles.

Referring to FIG. 9, there is depicted an embodiment of a urine guard, generally designated 160, fashioned as a bib or the like that may be used during bathing of the infant or otherwise. The guard 160 has a body 162 formed from a soft, pliable, liquid-absorbent material that may be a natural fiber such as cotton or the like, a man-made fiber or a combination of natural and man-made fibers. The body 162 may be a single layer of material or may be two or more (multiple) layers of material. In a washable (and this re-usable) form, the body 162 may be formed of terry-cloth. In a disposable form, the body 162 may be formed of a disposable-type wash-cloth material such as is known in the art. Cording 164 is provided on the perimeter of the body 162. The bib features may be incorporated into the various bath time versions of the present urine guard.

The body 162 has a lower appendage 166 that is shaped to cover the groin or groin area of an infant. A first ballast 168 extends from one side of the body 162, while a second ballast 170 extends from another side of the body 162 opposite to that of the first ballast 168. Each ballast 168, 170 preferably, but not necessarily, has the same shape. The ballasts 168 and 170 stabilize the guard when placed over an infant. The body 162 further defines a neck cutout 172 formed between two upper portions 173, 174. The upper portions 173, 174 are configured to lie on/over the shoulders of the infant.

In this embodiment, the shape of the ballasts 168, 170 not only provide stability for the guard when place on the infant, but allows the ballasts 168, 170 to aid in washing of the infant. The additional material of the bib version provides warmth and comfort to an infant during the bath. The side ballasts provide simultaneous stability to hold the urine guard in place during the bath. The side ballasts are formed of the same soft liquid absorbable material that is safe and effective to use to wash the infant during a bath. When used dry, the material is such as to provide effective drying of the infant immediately after a bath.

The various guards of FIGS. 7-9 are contoured or designed such that they naturally lie and stay on the infant during use. The ballasts or flaps provide additional ballast or weight that holds the guards into place during use. Moreover, the guards of FIGS. 7-9 are particularly suitable for use during bathing. When wet, the guards cling to the infant due to their weight. The wet ballasts, again, provide extra weight to maintain the guard on the infant.

It should be appreciated that the bath time urine guard of FIGS. 7-9 while formed of a washable, liquid absorbable material for the various parts they may particularly be formed, entirely, partially or substantially of an eco-friendly and/or easily renewable material such as bamboo, hemp or the like. Bamboo for instance, has four (4) times more absorbency than cotton, is naturally anti-fungal and antimicrobial, and can be Mercerized for extra strength and long life. A disposable version may also be made of the bath time urine guard. In this case, eco-friendly, non-cloth, biodegradable materials are used for this purpose. It would be economically feasible and environmentally responsible or friendly and could be environmentally beneficial to dispose of the disposable bath time urine guard after one use or soiling. This would find use in hospital and daycare settings. Waste methods could include but not be limited to landfills, composting or flushing down a toilet. The material could therefore contain a composition that is beneficial to the environment and/or helps aid in decomposition such as, but not limited to, a plant based material or food based material (e.g. cornstarch). The materials may include nutrients and/or components that are biodegradable and beneficial to the soil (e.g. fluffed wood pulp and viscose rayon, both of which are harvested from trees under the Sustainable Forestry Initiative established in 1994).

Sodium polyacrylate crystals (known as "super absorbent polymer" or SAP) are another option available to form the current bath time urine guard such as are used in disposable diapers, and which can hold one hundred times their weight in water. Because of the absorbent properties of SAP, these crystals can be added to compost and biosolids to increase moisture retention and enrich soil. Biodegradable natural and recycled polymers may also be used.

Figure 10:
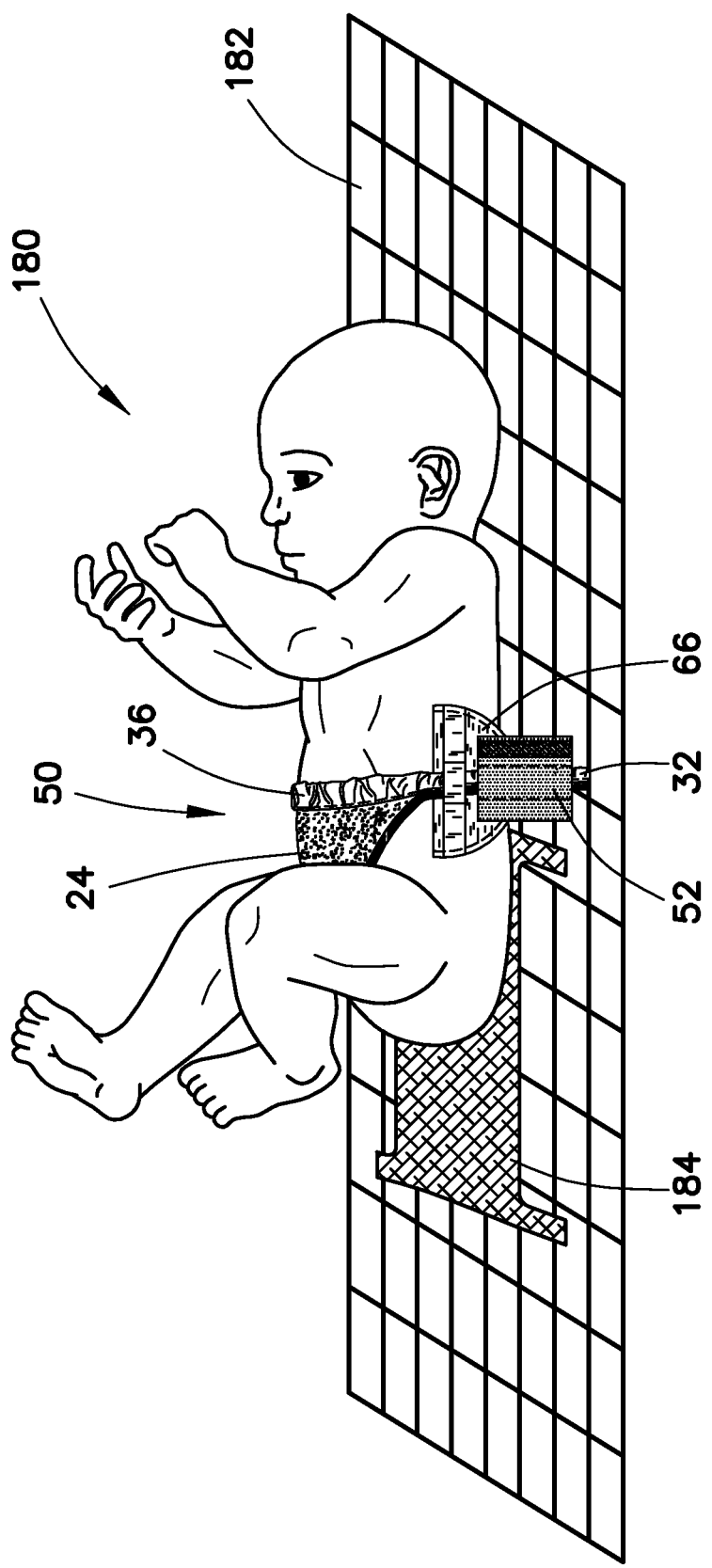
FIG. 10 is a perspective view of an infant for which a urine guard is being used while changing the infant's diaper.

In accordance with an aspect of the present invention, a diaper changing methodology is provided utilizing the present urine guard. For reference, attention is directed to FIG. 10 wherein a baby 180 is shown on a changing mat 182 whose diaper is to be changed. FIG. 10 also illustrates how the present urine guard is used. With respect to a diaper changing methodology utilizing the present invention, initially, clothing, except the diaper to be changed, is removed from or taken out of the way of the waist area and below. While the baby 180 in FIG. 10 is shown without clothes on the torso thereof, it should be appreciated that clothes above the waist may remain during the present diaper changing process. After the diaper area of the baby has been cleared of clothing, a clean diaper 184 is placed under the soiled diaper (still disposed on baby but not shown). The urine guard 50 (representing any one of the guard embodiments presented herein) is then placed over the abdomen of the baby.

Particularly, each elongated end 30, 32 (of which only elongated end 32 is seen in FIG. 10) of the guard 50 is stretched or placed over the infant 180 such that the sheathed elastic 36 is over the midsection of the infant and the shield 24 of the guard 50 is over the groin (and thus genitals) of the infant. Each end structure 52, 54 (of which only end structure 52 is seen in FIG. 10) is positioned on its respective elongated end 32, 30 as appropriate to be able to releasably attach the end structure to the changing mat 182. While not shown, the end structures 52, 54 may alternatively be attached to the clean diaper rather than to the mat 182 (if there is no mat or it is not desired to attach the ends of the urine guard to the mat). In either case, the elastic portion 34 of the urine guard allows the elongated ends/end structures thereof to extend beyond the sides of the baby and onto the mat. The side pads 66, 68 (of which only one side pad 66 is seen in FIG. 10) are adjusted so as to engage the sides of the baby.

Thereafter, the soiled diaper is loosened in front and the baby cleaned up. The soiled diaper is then removed. All the time the guard 50 is in place to catch or absorb any urine that may discharge from the infant 180. The guard 50 is then removed. Thereafter, the clean diaper is then fastened in place.

It should be appreciated that one or more embodiments of the present urine guard may be used during bathing of the infant or otherwise as appropriate. Moreover, the use of the terms "first" and "second" is arbitrary.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A one size fits all, entirely machine washable and thus reusable urine guard for receiving urine discharging from an infant during diaper change, the urine guard comprising:
   a shield formed of a liquid absorbable, machine washable and thus reusable material sized to extend from a waist area of an infant to and over a front groin area of the infant during use;
   a supple and elastically stretchable continuous waistband formed of a machine washable and thus reusable material that is permanently attached to and extends along an entire upper end of the shield, the waistband having a first elongated end integral with and extending from a first upper side of the upper end of the shield, the first elongated end having a length that is sufficient to reach by stretching a distance along an object situated under a first side of the infant, and a second elongated end integral with and extending from a second upper side of the upper end of the shield, the second elongated end having a length that is sufficient to reach by stretching a distance along an object situated under a second side of the infant;
   a sheath covering the entire waistband and formed of a machine washable and thus reusable material;

a first removable hook and loop style fastener configured as a first tab made of a machine washable and thus reusable material disposed on a free end of the first elongated end and adapted for releasable attachment to the object situated under the first side of the infant via a first hook style fastening portion situated on a back side of the first tab, the first hook style fastener portion configured to be selectively completely enclosed by the first tab via a first loop style fastening portion disposed on a front side of the first tab such that when the first tab is folded about the first elongated end, the first loop style fastening portion attaches to the first hook style fastener portion;

a second removable hook and loop style fastener configured as a second tab made of a machine washable and thus reusable material disposed on a free end of the second elongated end and adapted for releasable attachment to the object situated under the second side of the infant via a second hook style fastening portion situated on a back side of the second tab, the second hook style fastener portion configured to be selectively completely enclosed by the second tab via a second loop style fastening portion disposed on a front side of the second tab such that when the second tab is folded about the second elongated end, the second loop style fastening portion attaches to the second hook style fastener portion;

a first solid side pad made of a machine washable and thus reusable material having a first external loop of the material that forms a first opening through which the first elongated end is received and which allows the first solid side pad to be adjustable along the length of the first elongated end and to be removable from the free end of the first elongated end; and a second solid side pad made of a machine washable and thus reusable material having a second external loop of the material that forms a second opening through which the second elongated end is received and which allows the second solid side pad to be adjustable along the length of the second elongated end and to be removable from the free end of the second elongated end.

2. The urine guard of claim 1, wherein the shield, the sheath and the first and second solid side pads are formed of a completely eco-friendly material.

3. The urine guard of claim 2, wherein the eco-friendly material is one of bamboo and hemp.

4. The urine guard of claim 2, wherein the shield, the sheath and the first and second solid side pads are formed of a biodegradable, completely eco-friendly disposable material.

5. The urine guard of claim 4, wherein the shield, the sheath and the first and second solid side pads formed of a biodegradable, completely eco-friendly disposable material that further has a composition that is beneficial to the environment during decomposition.

6. The urine guard of claim 5, wherein the composition that is beneficial to the environment comprises one of fluffed wood pulp and viscose rayon.

7. A one size fits all, entirely machine washable and thus reusable urine guard for receiving urine discharging from an infant during diaper change, the urine guard comprising:

a shield formed of a liquid absorbable, machine washable and thus reusable material sized to extend from a belly button area of an infant to and over a front groin area of the infant during use;

a supple and elastically stretchable continuous waistband formed of a machine washable and thus reusable material that is permanently attached at an intermediate portion of the shield and extends along an entire upper end of the shield, the waistband having a first elongated end extending from a first upper side of the upper end of the shield and having a length that is sufficient to reach by stretching a distance along an object situated under a first side of the infant, and a second elongated end extending from a second upper side of the upper end of the shield and having a length that is sufficient to reach by stretching a distance along an object situated under a second side of the infant;

a supple sheath covering the entire waistband and formed of a machine washable and thus reusable material;

a first removable hook and loop style fastener configured as a first tab made of a machine washable and thus reusable material disposed on a free end of the first elongated end and adapted for releasable attachment to the object situated under the first side of the infant via a first hook style fastening portion situated on a back side of the first tab in order to hold first elongated end onto the object situated under the first side of the infant, the first removable hook and loop style fastener configured to be selectively completely enclosed by the first tab via a first loop style fastening portion disposed on a front side of the first tab such that when the first tab is folded about the first elongated end the first loop style fastening portion attaches to the first hook style fastener portion;

a second removable hook and loop style fastener configured as a second tab made of a machine washable and thus reusable material disposed on a free end of the second elongated end and adapted for releasable attachment to the object situated under the second side of the infant via a second hook style fastening portion situated on a back side of the second tab in order to hold second elongated end onto the object situated under the second side of the infant, the second removable hook and loop style fastener configured to be selectively completely enclosed by the second tab via a second loop style fastening portion disposed on a front side of the second tab such that when the second tab is folded about the second elongated end the second loop style fastening portion attaches to the second hook style fastener portion;

a first solid side pad made of a machine washable and thus reusable material having a first external loop of the material forming a first opening through which the first elongated end is received and which allows the first solid side pad to be adjustable along the length of the first elongated end and to be removable from the free end of the first elongated end; and a second solid side pad made of a machine washable and thus reusable material having a second external loop of the material forming a second opening through which the second elongated end is received and which allows the second solid side pad to be adjustable along the length of the second elongated end and to be removable from the free end of the second elongated end.

8. The urine guard of claim 7, wherein the shield, the sheath and the first and second solid side pads are formed of a completely eco-friendly material.

9. The urine guard of claim 8, wherein the eco-friendly material is one of bamboo and hemp.

10. The urine guard of claim 8, wherein the shield, the sheath and the first and second solid side pads are formed of a biodegradable, completely eco-friendly disposable material.

11. The urine guard of claim 10, wherein the shield, the sheath and the first and second solid side pads formed of a biodegradable, completely eco-friendly disposable material that further has a composition that is beneficial to the environment during decomposition.

12. The urine guard of claim 11, wherein the composition that is beneficial to the environment comprises one of fluffed wood pulp and viscose rayon.

\* \* \* \* \*